(12) United States Patent
Nupnau et al.

(10) Patent No.: US 8,591,740 B2
(45) Date of Patent: Nov. 26, 2013

(54) METHOD AND SYSTEM FOR BIOFOULING CONTROL OF SHIPBOARD COMPONENTS

(75) Inventors: Lars Nupnau, Mountainside, NJ (US);
Michael Upjohn, Llandogo (GB);
Vadim Zolotarsky, Springfield, NJ (US)

(73) Assignee: Siemens Water Technologies LLC, Alpharetta, GA (US)

( * ) Notice: Subject to any disclaimer, the term of this patent is extended or adjusted under 35 U.S.C. 154(b) by 282 days.

(21) Appl. No.: 13/059,357

(22) PCT Filed: Aug. 18, 2009

(86) PCT No.: PCT/US2009/054172
§ 371 (c)(1),
(2), (4) Date: Feb. 16, 2011

(87) PCT Pub. No.: WO2010/022057
PCT Pub. Date: Feb. 25, 2010

(65) Prior Publication Data
US 2011/0139729 A1    Jun. 16, 2011

Related U.S. Application Data

(60) Provisional application No. 61/089,885, filed on Aug. 18, 2008.

(51) Int. Cl.
| | |
|---|---|
| B01D 61/16 | (2006.01) |
| B01D 65/02 | (2006.01) |
| B01D 65/08 | (2006.01) |
| B01D 35/16 | (2006.01) |
| C02F 1/46 | (2006.01) |
| C02F 1/50 | (2006.01) |
| C02F 1/76 | (2006.01) |

(52) U.S. Cl.
USPC ... 210/636; 210/170.11; 210/202; 210/257.1; 210/259; 210/321.69; 210/411; 210/639; 210/747.5; 210/748.12; 210/748.2; 210/754; 210/764

(58) Field of Classification Search
USPC ............... 210/170.11, 192, 198.1, 202, 203, 210/257.1, 258, 259, 739, 748.01, 74, 8.1, 210/748.11, 748.12, 748.16, 748.17, 748.2, 210/747.5, 754, 764, 321.69, 636, 108, 210/321.6, 411, 639, 650, 651, 791, 797, 210/798; 422/24, 28, 29, 37, 186.3
See application file for complete search history.

(56) References Cited

U.S. PATENT DOCUMENTS

| | | | | |
|---|---|---|---|---|
| 3,577,341 | A * | 5/1971 | Keith et al. | 210/712 |
| 4,986,918 | A * | 1/1991 | Breslau et al. | 210/652 |
| 6,001,254 | A * | 12/1999 | Espenan et al. | 210/636 |
| 6,183,646 | B1 * | 2/2001 | Williams et al. | 210/636 |
| 6,613,232 | B2 * | 9/2003 | Chesner et al. | 210/650 |
| 6,773,611 | B2 * | 8/2004 | Perlich et al. | 210/758 |

(Continued)

OTHER PUBLICATIONS

International Search Report and Written Opinion, Publication No. PCT/US 09/54172, dated Oct. 13, 2009, 8 pages.

Primary Examiner — Joseph Drodge

(57) ABSTRACT

A chlorine based biofouling control subsystem is utilized to facilitate shipboard water management systems such as ballast water management that employ filters. The biofouling control system can serve as a subsystem to promote antifouling and reduce the filter clogging due to biofouling, which improves the efficiency and effectiveness of the ballast water treatment management system. An antifouling agent of the biofouling control system breaks up the dense colonies of marine organisms being filtered or treated by the main water management systems.

21 Claims, 5 Drawing Sheets

(56) References Cited

U.S. PATENT DOCUMENTS

| | | |
|---|---|---|
| 7,241,390 B2 | 7/2007 | Lyles |
| 7,455,022 B2 | 11/2008 | Randall |
| 2004/0099608 A1* | 5/2004 | Leffler et al. ............ 210/704 |
| 2005/0016933 A1 | 1/2005 | Perlich et al. |
| 2007/0181496 A1* | 8/2007 | Zuback ............ 210/636 |
| 2008/0000775 A1 | 1/2008 | Childers et al. |

* cited by examiner

METHOD AND SYSTEM FOR BIOFOULING CONTROL OF SHIPBOARD COMPONENTS

BACKGROUND

1. Field of Invention

This application is a 371 of PCT/US2009/054172 Aug. 18, 2009 which claims benefit of 61/089,885 Aug. 18, 2008 and relates to systems and methods biofouling control of components or systems exposed to seawater and, in particular, to biofouling control of components of seawater disinfection systems that treat ballast water.

2. Discussion of Related Art

Chlorine based disinfection systems typically utilize any of dry chlorine gas, bulk sodium hypochlorite, and in-situ chlorine or sodium hypochlorite electrolytic generators. The electrolysis of seawater to produce chlorine has been used in land-based industrial and offshore applications for biofouling control of cooling systems, such as systems that utilize seawater as a coolant. The development of self-cleaning tube-in-tube electrochemical cells has resulted in use of electrochlorination in shipboard applications, such as for biofouling control of engine cooling system, and air conditioning and other auxiliary systems.

A typical system layout for a land based chlorination system is schematically presented in FIG. 1A. Seawater is taken from a water intake or source 1 and pumped through an electrolytic generator 3 by a pump 2. The outlet of generator 3 containing a biocidal agent is delivered into a storage tank 5. A power supply 4 provides electrical current to electrolytic chlorine generator 3.

Storage tank 5 is typically equipped with one or more air blowers 6 that provide dilution or dispersion of a hydrogen gas by-product to a safe concentration. Direct hydrogen removal can be effected with hydrocyclones instead of the air blowers and tanks. Land based systems can produce hypochlorite solutions at relatively high concentrations, in a range of about 500 ppm to 2,000 ppm chlorine. One or more dosing pumps 7 can be utilized to dose chlorine to a point of use typically by way of a distribution device 8. The point of use is typically an intake basin, which provides water to another process such as, but not limited to, a cooling loop 9.

In some applications, dechlorination systems and techniques may be utilized, which can have an oxidizer-neutralizing agent, such as sodium bisulfite, for downstream treatment of the potable water or cooling water, prior to discharge to the environment or use thereof.

Ships use ballast water tanks to provide stability and maneuverability. Typically, ballast tanks are filled with water at one port after or during cargo unloading operations. The ballast water may be discharged at another port if cargo is loaded. Effectively, the ballast water would be transferred from the first port to the second port, with a potential for the introduction of aquatic nuisance species (ANS) at the second port. ANS transfer can be a detrimental ecological issue.

Shipboard electrochlorination systems, as schematically illustrated in FIG. 1B, are typically configured for low chlorine output with direct injection of chlorinated water. In shipboard electrochlorination systems, seawater is typically delivered from a sea chest 10 or a main using a booster pump 2 to one or more electrolytic generators 3. Each of the one or more generators 3 is typically powered by one or more power supplies 4. A product stream from generator 3 can be injected into sea chest 10 through a distribution device 8. In shipboard systems, cooling water is typically discharged outboard D and can be de-chlorinated by introducing an neutralizing agent, such as sodium bisulfite, from a source 11 to reduce the chlorine concentration therein to an allowable discharge level, typically less than 0.1 ppm.

Typically, a chlorine analyzer is utilized to monitor and maintain a concentration of residual chlorine in treated water.

SUMMARY OF THE INVENTION

A system is disclosed for providing biofouling control to the filtering equipment installed on shipboard as a part of, for example, a ballast water management system. Biofouling control provides protection to the filter against clogging beyond its self-cleaning capabilities and improves ballast water treatment by breaking up colonies of the marine organisms prior to their treatment.

One or more aspects of the invention can involve a biofouling control system for a filter upstream of a shipboard disinfection system. The biofouling control system can comprise a source of seawater fluidly connected upstream of the filter; a source of antifouling species configured to introduce at least one chlorine-based antifouling species into the seawater to be filtered; a controller configured to regulate introduction of the at least one chlorine-based antifouling species into the seawater to be filtered to provide a target antifouling concentration therein in a range of from 0.1 mg/L to 0.5 mg/L, as chlorine. The biofouling control system can further have a sensor disposed to measure a concentration of chlorine-based antifouling species in the seawater to be filtered, and provide a representation of the measured concentration to the controller. The shipboard disinfection system can be at least one of an ultraviolet irradiation system and a chlorination system. The biofouling control system can further comprise a flow sensor disposed to measure a flow rate of the seawater to be filtered, and to provide a representation of the measured flow rate to the controller. The controller is typically configured to generate an output signal based at least partially on the measured flow rate, and is further configured to transmit the output signal to the source of antifouling species. The biofouling control system can further comprise a pump disposed to withdraw seawater to be filtered from the source of seawater and introduce the seawater to be filtered into the filter, and wherein the source of antifouling species is configured to introduce the at least one chlorine-based antifouling species into the seawater to be filtered at a location downstream of the pump. Preferred configurations can involve systems with a target antifouling concentration in a range of 0.05 mg/L to 0.6 mg/L, from about 0.05 mg/L to 0.5 mg/L, but more preferred configurations involve a target antifouling concentration in a range of 0.1 mg/L to 0.3 mg/L. The biofouling control system can further comprise a backwash line fluidly connecting an outlet of the pump to an outlet of the filter. Further, the outlet of the filter can be fluidly connected upstream of at least one of an ultraviolet disinfecting system, a ship water cooling system, and a ship ballast tank. Further preferred configurations involve biofouling control of filters with a filtration size in a range of 10 μm to 50 μm. Particular configurations of the biofouling control system involve cases wherein the source of antifouling species comprises an electrolytic chlorine generator.

One or more aspects of the invention can involve a method of reducing biofouling of a filter upstream of a shipboard disinfection system. The method can comprise introducing seawater into the filter; introducing at least one chlorine-based antifouling species into seawater to be filtered at a target antifouling concentration to produce filtered seawater; and introducing filtered seawater into the shipboard disinfection system. The target antifouling concentration is in a range of 0.05 mg/L to 0.6 mg/L, but in some cases from about 0.05 mg/L to 0.5 mg/L, in the seawater to be filtered. The target antifouling concentration is preferably in a range of 0.2 mg/L to 0.3 mg/L in the seawater to be filtered. The method typically further comprises electrolytically generating the at least one chlorine-based antifouling species from seawater. Where suitable, introducing seawater into the filter comprises removing at least a portion of suspended particles having at least one dimension of at least about 10 μm from the seawater to be filtered. Other configurations involve filters that remove particles that are at least about 20 microns. For example, the method can involve utilizing filters with a screen in a size range of from 10 μm to 50 μm. The method typically further comprises electrolytically generating the at least one chlorine-based antifouling species from seawater; and backwashing the filter with seawater, which can be filtered seawater. The method can further comprise measuring a flow rate of the seawater to be filtered; and adjusting a rate of introduction of the at least one chlorine-based antifouling species into the seawater to be filtered based at least partially on the measured flow rate of the seawater to be filtered.

One or more aspects of the invention can involve a method of modifying an existing shipboard disinfection system having a filter. This method can comprise disposing a source of a chlorine-based antifouling species on a ship, the source of the chlorine-based antifouling species comprising an electrolytic generator; connecting an outlet of the electrolytic generator upstream of the filter of the shipboard disinfection system; configuring the electrolytic generator to provide at least one chlorine-based antifouling species into seawater to be filtered based at least partially on the rate of flow of seawater to be introduced into the filter. The method also can further comprise configuring the electrolytic generator to provide the at least one chlorine-based antifouling species into the seawater to be filtered to provide a target antifouling concentration therein in a range of from 0.05 mg/L to 0.6 mg/L, preferably from 0.05 mg/L to 0.5 mg/L, from 0.2 mg/L to 0.3 mg/L. Also in this embodiment of a method of the invention, configuring the electrolytic generator to provide the at least one chlorine-based antifouling species comprises connecting a controller to the electrolytic generator. Preferably, the controller can regulate the electrolytic generator based at least partially on a measured flow rate of the seawater to be filtered. Thus, in some instances, the method can comprise installing a controller configured to have an input port that can communicate with a flow meter disposed to measure a flow rate of the seawater to be introduced into the filter, such as at a location upstream of the filter.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing.

In the drawings.

DETAILED DESCRIPTION

Figure 1A:
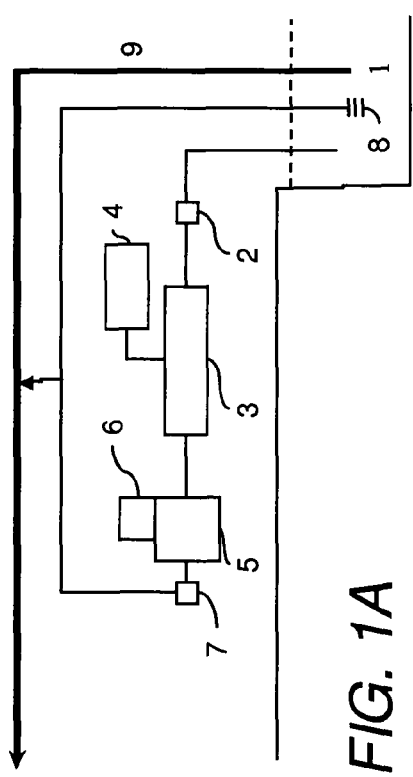
FIGS. 1A and 1B are schematic illustrations of land-based (FIG. 1A) and shipboard (FIG. 1B) water management systems.
Figure 1B:
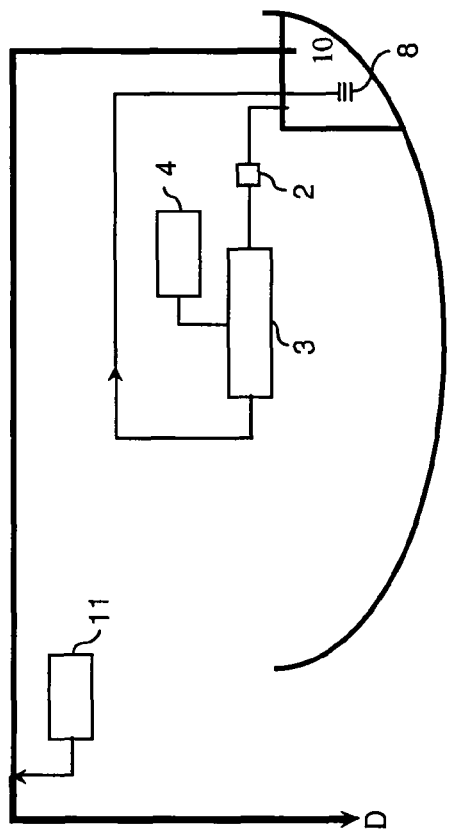

Marine organisms, such as zooplankton or phytoplankton, are typically difficult to kill or inactivate using biocides and or ultraviolet (UV) irradiation. Therefore, filtration systems are typically utilized, with 50 micron or less size filters, to remove at least a portion of zooplankton prior to the primary methods of treatment. Filtration systems are typically a prerequisite for some treatment approaches, such as in UV-based systems, because filters improve efficiency of actinic radiation-based systems by reducing turbidity of the seawater to be treated. The present invention further facilitates treatment operations by reducing biofouling of filtration systems, and can serve to improve the operational efficiency of filtration systems, even those equipped with self-cleaning techniques, such as those that utilize backwashing and self-flushing, because increased operational filtration availability can be realized.

Ballast water management systems of a ship are typically classified as utilizing active substances or ones that do not use any active substances. Systems that use active substance typically introduce an agent, e.g., a biocide, such as any one or more of hypochlorite, chlorine dioxide, hydrogen peroxide, and peracetic acid, and products of the advanced oxidation processes that inactivate biological organisms, typically microorganisms, in the ballast water. Systems that do not use active substances typically employ ultraviolet (UV) irradiation to inactivate the biological microorganisms.

Nonetheless, both approaches typically use filters to remove particulates, such as suspended microorganisms or even colonies of microorganisms prior to treatment in the water management system with active substances or other conventional disinfection or biocidal techniques. Typically, the screen size of the filter is in the range of 20 μm to 50 μm. Thus, because the filter is typically upstream of the treating system, it can be susceptible to biofouling. Because these filters may be prone to biofouling, and in some cases, such as during algae bloom, the filter may be completely blocked from filtering the seawater, which may endanger the ship safety, significantly delay loading and unloading operations, and can render the water treatment systems ineffective.

Conventional approaches that address biofouling of the filter typically involve, for example, backwashing the filter. Further, filters can be configured to be self-cleaning, to provide continual operation. In some cases, however, conventional approaches against biofouling cannot be redeemed using standards methods of backwashing, thus the filters will have to be cleaned manually.

The present invention is directed to a method and a system that controls or reduces biofouling to certain elements or components of a shipboard water management system or a shipboard disinfection system, such as the ballast water management system. In some cases, the present approach supplements existing seawater management systems by providing biofouling control of components thereof, such as filters.

Figure 2:
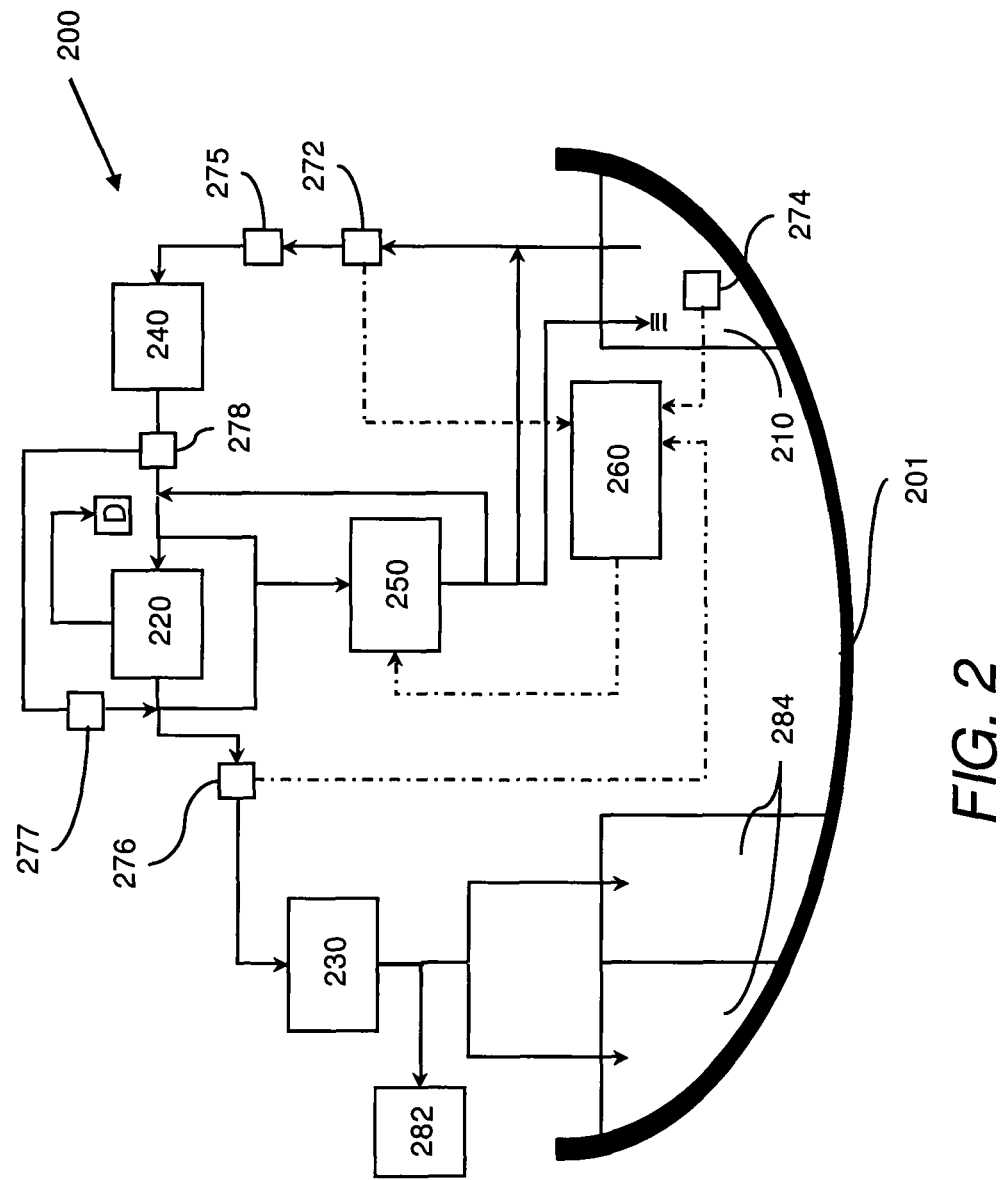
FIG. 2 is a schematic illustration of a biofouling control system in accordance with one or more aspects of the invention.

For example, one or more aspects of the invention can involve a ship's 201 biofouling control system 200 for a filter 220 that is disposed upstream of a shipboard seawater management system 230, as exemplarily presented in FIG. 2. The biofouling control system 200 can comprise a source of seawater 210 fluidly connected upstream of filter 220, a source of at least one antifouling species 250 configured to introduce at least one chlorine-based antifouling species into the seawater to be filtered, and a controller 260 configured to regulate introduction of the at least one chlorine-based antifouling species from source 250 into the seawater to be filtered, such as at source 210.

Water management system 230 can be a disinfection or treatment system. Particular configurations of the shipboard water management system can utilize any of the active approaches that involve introducing at least one biocidal agent selected from the group consisting of hypochlorite, chlorine dioxide, hydrogen peroxide and peracetic acid, products of, for example, an advanced oxidation process, and agents that can inactivate biological microorganisms in seawater. In other cases, the water management system utilizes at least one of an ultraviolet irradiation system and a chlorination system.

The biofouling control system can further have one or more sensors 272, 274, and 276 disposed to measure a concentration of chlorine-based antifouling species in the seawater to be filtered at any one or more of a location within the source 210 of seawater, within a line connecting the source of seawater to an inlet of pump 240, within a line connecting an outlet of pump 240 to an inlet of filter 220, and within a line from an outlet of filtered seawater from filter 240, and provide a representation of the measured concentration of the one or more antifouling species in the seawater, to controller 260.

The biofouling control system can further comprise one or more flow sensors 275 disposed to measure a flow rate of the seawater to be filtered, and to provide a representation of the measured flow rate to controller 260.

Preferably, the biofouling control system is configured to provide a target antifouling concentration of the antifouling species in the seawater to be treated or filtered that is in a range of from 0.1 mg/L to 0.6 mg/L, typically as chlorine. Controller 260 is typically configured to generate an output signal based at least partially on the measured flow rate, and is further configured to transmit the output signal to the source 250 of the one or more antifouling species. In some cases, controller 260 is configured to generate an output signal and transmit the output signal to source 250 and regulate the operation thereof to achieve the desired or target antifouling species concentration in the seawater to be treated. Preferred configurations can involve systems with a target antifouling species concentration in the seawater to be filtered that is in a range of 0.05 mg/L to 0.6 mg/L, but more preferred configurations involve a target antifouling species concentration that is in a range of 0.1 mg/L to 0.3 mg/L.

Source of antifouling species 250 can also optionally or alternatively be configured to introduce the at least one chlorine-based antifouling species into the seawater to be filtered at a location downstream of pump 250, but preferably also upstream of filter 220.

The biofouling control system can further comprise a backwash line fluidly connecting an outlet of pump 240 to an outlet of filter 220. The backwash from the filter can be discharged overboard D. The backwash line can be utilized during backwashing operations to facilitate cleaning or unclogging of filter 220 by introducing water in an opposite or reverse direction relative to the fluid flow direction during filtering operations. For example, controller 260 can be utilized to divert flow from the forward, filtering direction to a reverse or backwashing direction by actuating one or more valves, such as valves 277 and 278. In other cases, backwashing can be performed utilizing residual pressure downstream of the filter. Backwashing operation may be initiated upon detection of a pressure differential across filter 220. For example, backwashing filter 220 may be commenced when a threshold differential pressure is at least 0.5 bar, or even in a range of from 1 psid to 20 psid. Other variants of one or more embodiments may involve periodical backwashing based at least partially on service or operating duration of filter 240. For example, backwashing may commence at least once per hour, at least once per day, and even once per week but in some cases, backwashing may be performed after five minutes of filtering operation, after ten minutes of filtering operation, or even after 30 minutes of filtering operation. Further variants, however, may involve manual actuation of the valves 277 and 278 to effect backwashing of filter 220. Backwashing may be performed for a predefined backwash period, such as for a period in a range of from one minute to twenty minutes.

Source of antifouling species 250 is preferably further configured to introduce the at least one chlorine-based antifouling species into the backwash line.

The outlet of filter 220 can be fluidly connected upstream of at least one of an ultraviolet disinfecting system, a ship water cooling system 282, and one or more ship ballast tanks 284.

Further preferred configurations involve biofouling control of filters with a filtration size in a range of 10 μm to 50 μm.

Particular configurations of the biofouling control system involve cases wherein the source of antifouling species comprises an electrolytic chlorine generator. The antifouling species source can comprise an electrolytic generator with, for example, bipolar concentric tube electrodes, one or more of the electrodes is typically positively-charged and one or more other electrodes is typically negatively-charged. One or more of the electrodes of the electrolytic generator can have a platinum coating and be operated at a suitable current density, typically not exceeding 3,500 A/m$^2$, preferably less than 2,000 A/m$^2$, to provide the chlorine-based antifouling species, which can be any of dissolved $Cl_2$ and HOCl, preferably without co-generating hydrogen. Non-limiting examples of generators include those commercially available as CHLOROPAC® electrolytic generators, from Siemens Water Technologies Corp., Union, N.J.

One or more aspects of the invention can involve a method of reducing biofouling of a filter upstream of a shipboard disinfection system. The method can comprise introducing seawater into the filter; introducing at least one chlorine-based antifouling species into seawater to be filtered at a target antifouling concentration to produce filtered seawater; and introducing filtered seawater into the shipboard disinfection system. The target antifouling concentration is in a range of 0.05 mg/L to 0.6 mg/L, or even 0.2 mg/L to 0.5 mg/L, in the seawater to be filtered. The target antifouling concentration is preferably in a range of 0.2 mg/L to 0.3 mg/L in the seawater to be filtered. The method typically further comprises electrolytically generating the at least one chlorine-based antifouling species from seawater. Where suitable, introducing seawater into the filter comprises removing at least a portion of suspended particles having at least one dimension of at least about 10 μm from the seawater to be filtered. Other configurations involve filters that remove particles that are at least about 20 microns. For example, the method can involve utilizing filters with a mesh in a size range of from 10 μm to 50 μm.

The method typically further comprises electrolytically generating the at least one chlorine-based antifouling species from seawater; and backwashing the filter with seawater, preferably also having at least one chlorine-based antifouling species therein at a concentration in a range of from 0.05 mg/L to 0.6 mg/L. The method can further comprise measuring a flow rate of the seawater to be filtered; and adjusting a rate of introduction of the at least one chlorine-based antifouling species into the seawater to be filtered based at least partially on the measured flow rate of the seawater to be filtered.

One or more aspects of the invention can involve a method of modifying an existing shipboard disinfection system having a filter. This method can comprise disposing a source of a chlorine-based antifouling species on a ship, the source of the chlorine-based antifouling species comprising an electrolytic generator; connecting an outlet of the electrolytic generator upstream of the filter of the shipboard disinfection system; configuring the electrolytic generator to provide at least one chlorine-based antifouling species into seawater to be filtered based at least partially on the rate of flow of seawater to be introduced into the filter. The method also can further comprise configuring the electrolytic generator to provide the at least one chlorine-based antifouling species into the seawater to be filtered to provide a target antifouling concentration therein in a range of from 0.05 mg/L to 0.6 mg/L, from about 0.05 mg/L to 0.5 mg/L, preferably in a range of from 0.2 mg/L to 0.5 mg/L. Also in this embodiment of a method of the invention, configuring the electrolytic generator to provide the at least one chlorine-based antifouling species comprises connecting a controller to the electrolytic generator. Preferably, the controller can regulate the electrolytic generator based at least partially on a measured flow rate of the seawater to be filtered. Thus, in some instances, the method can comprise installing a controller configured to have an input port that can communicate with a flow meter disposed to measure a flow rate of the seawater to be introduced into the filter, such as at a location upstream of the filter.

The various embodiments of the present invention thus provide a system and process that injects a relatively small amount of biocide as an antifouling agent, preferably a halogen produced directly from seawater, at concentration levels that would minimize any potential impact to the crew and the environment, and have no harmful effect on the elements of the ballast water management system.

Other approaches that may be utilized in any of the systems and methods of the present invention may involve biofouling control systems that use a fixed biocide dose level, or a variable biocide dose level controlled based at least partially on any one of, for example, oxidation-reduction potential (ORP) and residual biocide analysis.

The water management system can also further comprise additional filtration stages that are configured to remove marine organisms that have typical dimensions greater than above 50 microns, and, optionally, pathogen-sized components. The present invention may be utilized to reduce any biofouling tendencies for any of the filtration stages that are typically disposed upstream of biocide or disinfection system 230.

Figure 3:
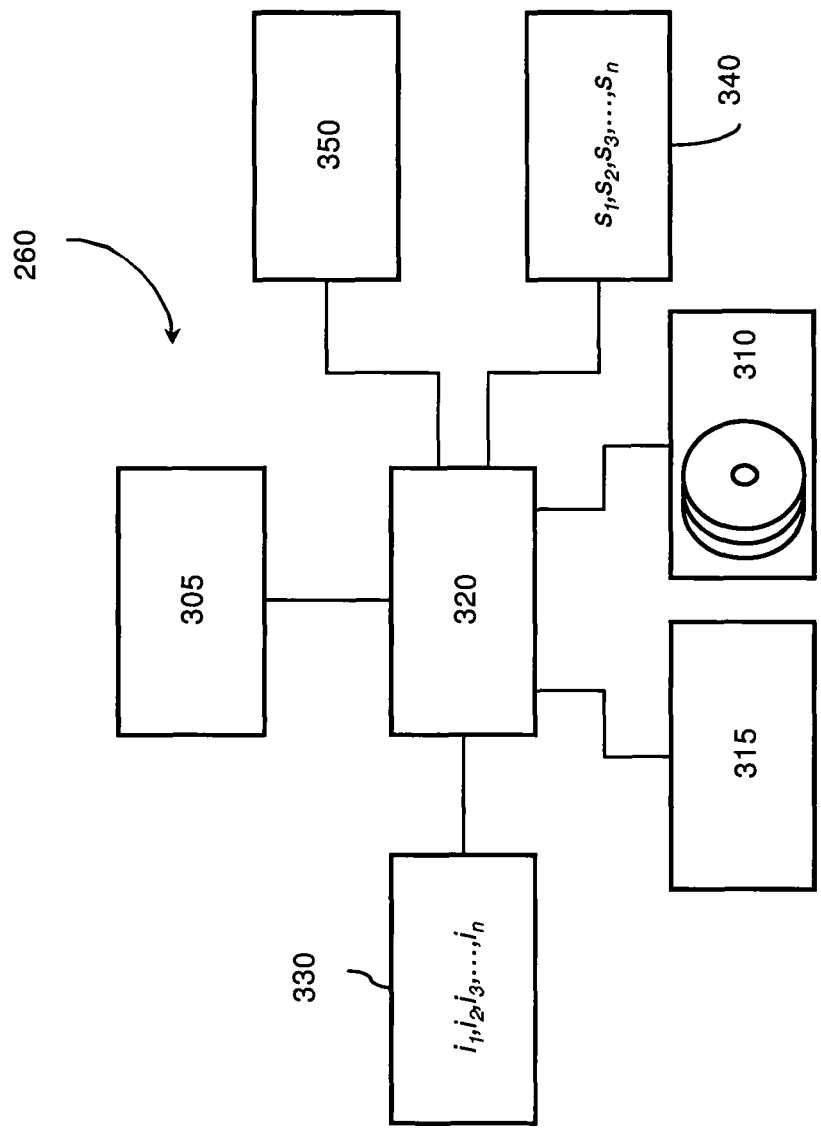
FIG. 3 illustrates a computer system upon which one or more embodiments of the invention may be practiced.

Controller 260 may be implemented using one or more computer systems as exemplarily shown in FIG. 3. Controller 260 may be, for example, a general-purpose computer such as those based on an Intel PENTIUM®-type processor, a Motorola PowerPC® processor, a Sun UltraSPARC® processor, a Hewlett-Packard PA-RISC® processor, or any other type of processor or combinations thereof. Alternatively, the computer system may include specially programmed, special-purpose hardware, for example, an application-specific integrated circuit (ASIC) or controllers intended for analytical systems. Controller 260 can include one or more processors 305 typically connected to one or more memory devices 310 and 315, which can comprise, for example, any one or more of a disk drive memory, a flash memory device, a RAM memory device, or other device for storing data. The one or more memory devices 310 and 315 are typically used for storing programs and data during operation of the biofouling control system and/or the water management system. For example, any of memory 310 or 315 may be used for storing historical data relating to the parameters over a period of time, as well as operating data. Software, including programming code that implements embodiments of the invention, can be stored on a computer readable and/or writeable nonvolatile recording medium, and then typically copied into memory wherein it can then be executed by the processor. Such programming code may be written in any of a plurality of programming languages, for example, Java, Visual Basic, C, C#, or C++, Fortran, Pascal, Eiffel, Basic, COBAL, or any of a variety of combinations thereof.

Components of the controller may be coupled by an interconnection mechanism 320, which may include one or more busses (e.g., between components that are integrated within a same device) and/or a network (e.g., between components that reside on separate discrete devices). The interconnection mechanism typically enables communications (e.g., data, instructions) to be exchanged between components of the system.

The controller can also include one or more input devices 330, for example, any of the sensors 272, 274, 276, and 275, a monitoring system, a keyboard, mouse, trackball, microphone, touch screen, that provide input signals $i_1, i_2, i_3, \ldots i_n$, and can provide output signals, $s_1, s_2, s_3, \ldots, s_l$, to one or more output devices 340 such as, but not limited to, generator 250, pump 240, a printing device, a display screen, a speaker, and valves 277 and 278. In addition, the controller may contain one or more interfaces 350 that can connect the computer system to a communication network (in addition or as an alternative to the network that may be formed by one or more of the components of the system).

According to one or more embodiments of the invention, the one or more input devices may include sensors for measuring parameters. Alternatively, the sensors, the metering or flow control valves and/or pumps, or all of these components may be connected to a communication network that is operatively coupled to a computer system. For example, the various sensors may be configured as input devices that are directly connected to the controller; and metering valves and/or pumps may be configured as output devices that are connected to the computer system, and any one or more of the above may be coupled to another computer system or component so as to communicate therewith over a communication network. Such a configuration permits one or more sensors to be located at a significant distance from another sensor or allow any sensor to be located at a significant distance from any subsystem and/or the controller, while still providing data therebetween.

Although the controller is shown by way of example as one type of computer system upon which various aspects of the invention may be practiced, it should be appreciated that the invention is not limited to being implemented in software, or on the computer system as exemplarily shown. Indeed, rather than implemented on, for example, a general purpose computer system, or components or subsections thereof, may alternatively be implemented as a dedicated system or as a dedicated programmable logic controller (PLC) or in a distributed control system. Further, it should be appreciated that one or more features or aspects of the invention may be implemented in software, hardware or firmware, or any combination thereof. For example, one or more segments of an algorithm executable by the controller can be performed in separate computers, which in turn, can be communication through one or more networks.

Co-pending U.S. patent application No. 61/089,885, titled "METHOD AND PROCESS FOR BIOFOULING CONTROL OF FILTERS USED IN BALLAST WATER TREATMENT," filed Aug. 18, 2008, is incorporated herein by reference in its entirety for all purposes.

EXAMPLES

The function and advantages of these and other embodiments of the invention can be further understood from the examples below, which illustrate the benefits and/or advantages of the one or more systems and techniques of the invention but do not exemplify the full scope of the invention.

Example 1

Ballast water with a flow rate of 200 m$^3$/hr of seawater was treated with a combination of filtration and chlorination technologies in a system exemplarily illustrated in FIG. 2.

The seawater was characterized as having a dissolved organic content of about 5 mg/L, a particulate organic content of about 5 mg/L, and a total suspended solids content of about 50 mg/L.

The ballast water flow was treated first upstream of the filter with about 0.11 m$^3$/h flow of chlorinated water with chlorine content of about 200 mg/L resulting in an apparent chlorine dose level of about 0.1 mg/L in the seawater to be filtered. The same chlorinated water was used to treat ballast water downstream of the filter at a rate of about 5.5 m$^3$/h, which resulted in an apparent chlorine dose level of about 5.5 mg/L.

Figure 4:
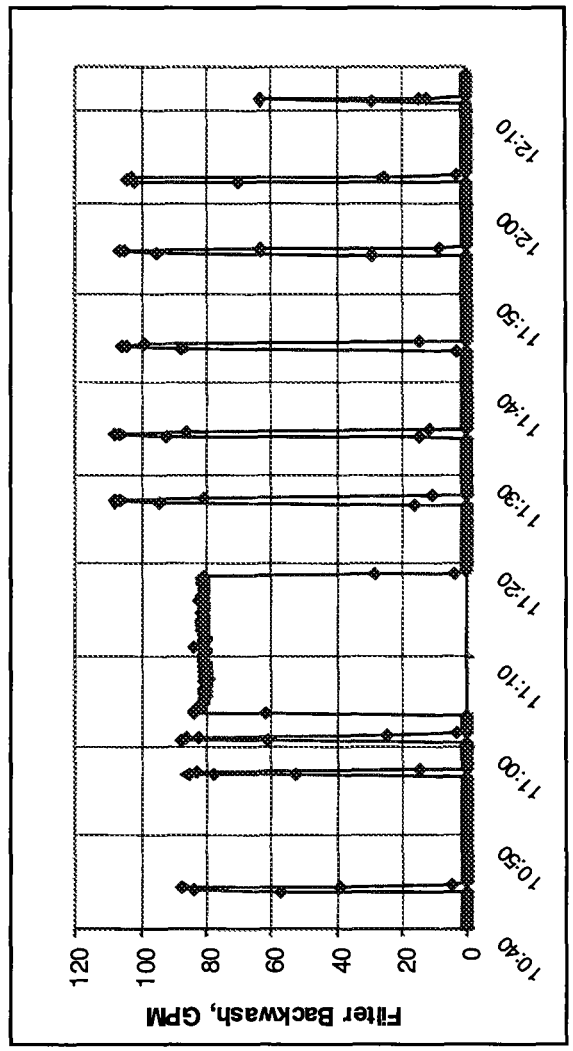
FIG. 4 is a graph showing filtration and backwashing duty cycle of a filter in accordance with one or more embodiments of the invention.

FIG. 4 shows the filtration and backwashing duty cycle of the filter with a differential pressure of 0.5 bar. During the 1.5-hour run, the filter was automatically switched to a 40-second backwash cycle every 8 to 10 minutes and once went into a continuous 15-minute backwash cycle, which generated an average backwash flow of 4.6 m$^3$/h.

Samples of backwash flow and the treated ballast water flow were collected and analyzed for a total residual oxidant (TRO) concentration and chlorination byproducts or disinfection byproducts (DBP), such as trihalomethanes (THM), and haloacetic acids (HAA). TRO in the backwash sample was found to be between 0.02 mg/L to 0.1 mg/L. The TRO of the treated water was found to be about 2 mg/L to about 3 mg/L. The results of DBP analysis are presented in the Tables 1 and 2.

TABLE 1

Concentration of Disinfection by-products (THM) in filter backwash flow.

| Disinfection byproduct<br>Trihalomethanes | Control<br>(μg/L)<br>Day 0 | Backwash<br>(μg/L)<br>Day 0 |
|---|---|---|
| Trichloromethane | <0.5 | <0.5 |
| Bromodichloromethane | <0.5 | 0.6 |
| Dibromochloromethane | <0.5 | 3.5 |
| Tribromomethane | <0.5 | 9.6 |

TABLE 2

Disinfection by-products (HAA) in filter backwash flow.

| Disinfection byproduct<br>Haloacetic Acids | Control<br>(μg/L)<br>Day 0 | Backwash<br>(μg/L)<br>Day 0 |
|---|---|---|
| Monochloroacetic acid | <2.0 | <2.0 |
| Dichloroacetic acid | <1.0 | <1.0 |
| Trichloroacetic acid | <1.0 | <1.0 |
| Bromochloroacetic acid | <1.0 | <1.0 |
| Monobromoacetic acid | <1.0 | <1.0 |
| Dibromoacetic acid | <1.0 | <1.0 |
| Tribromoacetic acid | <4.0 | <4.0 |

The data shows that there is enough TRO in the filter to provide biofouling control even at chlorine dosing levels of just 0.1 mg/L. At this level, the concentration of disinfection by-products in backwash flow is very low and should not present any environmental or other risk during discharge overboard. Only bromoform was found present in the backwash flow in more or less significant quantity; however, its concentration is lower than a Predicted No-Effect Concentration (PNEC) for this chemical species. Therefore, even without taking into account its dilution in the coastal water after discharge, the DBP should not harm the environment.

Example 2

Figure 5B:
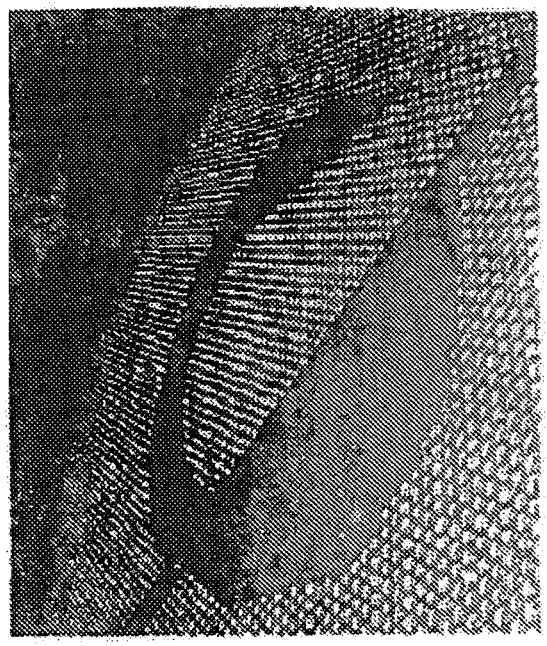
FIGS. 5A and 5B are reproductions of photographs showing the effects of utilizing (FIG. 5B) and not utilizing (FIG. 5A) the antifouling features of the invention on a heat exchanger of a shipboard cooling system.
Figure 5A:
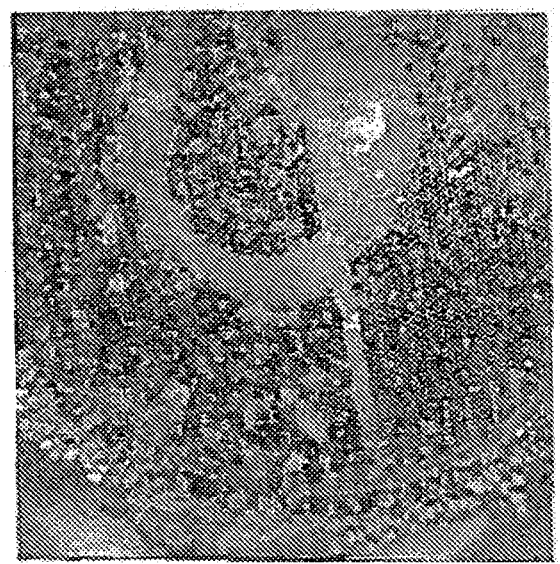

FIGS. 5A and 5B illustrates an appearance of the ship's main engine's heat exchanger plate without (FIG. 5A) and with biofouling control system (FIG. 5B) as employed in accordance with the present invention to address biofouling problems. Biofouling control was provided using a CHLOROPAC® biofouling control system manufactured by Siemens Water Technologies Corp. This system can produce hypochlorite from seawater by using principles of electrochemistry and doses the generated hypochlorite into the sea chest that feeds the cooling water main. The hypochlorite dosing level is typically in a range of 0.05 mg/L to 0.6 mg/L. The comparison shows the effectiveness of this system in maintaining the heat-exchanger surface free of any biological debris.

Use of a low-level antifouling agent, less than 0.6 mg/L, typically in a range of between 0.05 mg/L to 0.5 mg/L, can maintain the surfaces of the heat exchangers and other cooling water equipment free of biofouling and does not carry any potential for corrosion or pollution. Unlike disinfection, low level biocide dosing for antifouling is suitable for this application and does not necessarily kill the marine organisms, but rather create an environment that is not suitable for their reproduction.

Ballast water management systems undergo a rigorous approval process that involves environmental risk characterization and assessment. Therefore, biofouling control using a biocide as an antifouling agent is not expected to contribute to any additional potential environmental risks.

With these considerations, the biofouling system for shipboard components, such as filters, for the ballast water management system can be designed to have a biocide concentration at the level minimally required to provide antifouling protection.

Having now described some illustrative embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention. In particular, although many of the examples presented herein involve specific combinations of method acts or system elements, it should be understood that those acts and those elements might be combined in other ways to accomplish the same objectives.

Those skilled in the art should appreciate that the parameters and configurations described herein are exemplary and that actual parameters and/or configurations will depend on the specific application in which the systems and techniques of the invention are used. Those skilled in the art should also recognize or be able to ascertain, using no more than routine experimentation, equivalents to the specific embodiments of the invention. It is therefore to be understood that the embodiments described herein are presented by way of example only and that, within the scope of the appended claims and equivalents thereto; the invention may be practiced otherwise than as specifically described.

Moreover, it should also be appreciated that the invention is directed to each feature, system, subsystem, or technique described herein and any combination of two or more features, systems, subsystems, or techniques described herein, and/or methods, if such features, systems, subsystems, and techniques are not mutually inconsistent, is considered to be within the scope of the invention as embodied in the claims. Further, acts, elements, and features discussed only in connection with one embodiment are not intended to be excluded from a similar role in other embodiments.

As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A biofouling control system upstream of a shipboard disinfection system comprising:
   a filter having an inlet, a filtered seawater outlet, and a pore size in a range of from about 10 micrometers to 50 micrometers;
   a source of seawater fluidly connected upstream of the filter;
   a pump disposed to withdraw seawater to be filtered from the source of seawater through an outlet of the pump fluidly connected to the inlet of the filter so as to introduce the seawater to be filtered into the filter through a first line;
   a backwash line fluidly connecting the outlet of the pump to the filtered seawater outlet of the filter and arranged to divert seawater from the first line and to direct seawater to the filtered seawater outlet of the filter as backwash liquid;
   a source of antifouling species configured to introduce at least one chlorine-based antifouling species into the seawater to be filtered; and
   a controller configured to regulate introduction of the at least one chlorine-based antifouling species into the seawater to be filtered to provide a target antifouling species concentration therein in a range of from about 0.05 mg/l to 0.5 mg/l, as chlorine.

2. The biofouling control system of claim 1, further comprising a sensor disposed to measure a concentration of the chlorine-based antifouling species in the seawater to be filtered, and provide a representation of the measured concentration thereof to the controller.

3. The biofouling control system of claim 1, wherein the shipboard disinfection system comprises at least one of an ultraviolet irradiation system and a chlorination system.

4. The biofouling control system of claim 1, further comprising a flow sensor disposed to measure a flow rate of the seawater to be filtered, and to provide a representation of the measured flow rate to the controller.

5. The biofouling control system of claim 4, wherein the controller is configured to generate an output signal based at least partially on the measured flow rate, and is further configured to transmit the output signal to the source of antifouling species.

6. The biofouling control system of claim 5, wherein the source of antifouling species is configured to introduce the at least one chlorine-based antifouling species into the seawater to be filtered at a location downstream of the pump.

7. The biofouling control system of claim 6, wherein the target antifouling species concentration is in a range of from 0.2 mg/l to 0.5 mg/l.

8. The biofouling control system of claim 6, wherein the target antifouling species concentration is in a range of from 0.1 mg/l to 0.3 mg/l.

9. The biofouling control system of claim 8, wherein the filtered seawater outlet of the filter is fluidly connected upstream of at least one of an ultraviolet disinfecting system, a ship water cooling system, and a ship ballast tank.

10. The biofouling control system of claim 9, wherein the source of antifouling species comprises an electrolytic chlorine generator.

11. The biofouling control system of claim 1, wherein the backwash line is arranged to direct filtered seawater to the filtered seawater outlet of the filter as backwash liquid.

12. A method of reducing biofouling of a shipboard disinfection system, the method comprising:
   introducing seawater to be filtered with a pump into a filter having an inlet, a filtered seawater outlet, and a pore size in a range of from about 10 micrometers to 50 micrometers;
   introducing at least one chlorine-based antifouling species into the seawater to be filtered at a target antifouling species concentration in a range of from about 0.05 mg/l to 0.5 mg/l to produce filtered seawater;
   introducing the filtered seawater into the shipboard disinfection system; and
   backwashing the filter with seawater directed from an outlet of the pump in fluid communication with the filter to the filtered seawater outlet of the filter and in a reverse direction through the filter relative to a direction of fluid flow during filtration of the seawater.

13. The method of claim 12, wherein the target antifouling species concentration is in a range of from 0.1 mg/l to 0.3 mg/l in the seawater to be filtered.

14. The method of claim 13, further comprising electrolytically generating the at least one chlorine-based antifouling species from seawater.

15. The method of claim 12, wherein the target antifouling species concentration is in a range of from 0.05 mg/l to 0.3 mg/l in the seawater to be treated.

16. The method of claim 12, wherein introducing seawater into the filter comprises removing at least a portion of suspended particles having at least one dimension of at least about 10 µm from the seawater to be filtered.

17. The method of claim 14, wherein backwashing the filter comprises backwashing the filter with seawater having at least one chlorine-based antifouling species therein at a concentration in a range of from 0.05 mg/l to 0.5 mg/l.

18. The method of claim 17, further comprising:
measuring a flow rate of the seawater to be filtered; and
adjusting a rate of introduction of the at least one chlorine-based antifouling species into the seawater to be filtered based at least partially on the measured flow rate of the seawater to be filtered.

19. A method of modifying an existing shipboard disinfection system including a filter having an inlet, a filtered seawater outlet, and a pore size in a range of from about 10 micrometers to 50 micrometers, the method comprising:
disposing a source of a chlorine-based antifouling species on a ship, the source of the chlorine-based antifouling species comprising an electrolytic generator;
connecting an outlet of the electrolytic generator upstream of the filter of the shipboard disinfection system;
configuring the electrolytic generator to provide at least one chlorine-based antifouling species into seawater to be filtered based at least partially on the rate of flow of seawater to be introduced into the filter at a target antifouling species concentration therein in a range of from about 0.05 mg/l to 0.5 mg/l; and
disposing a backwash line in fluid communication with the filtered seawater outlet of the filter, the backwash line arranged to direct seawater diverted from the filter inlet to the backwash line as backwash liquid through the filter.

20. The method of claim 19, further comprising configuring the electrolytic generator to provide the at least one chlorine-based antifouling species into the seawater to be filtered to provide a target antifouling concentration therein in a range of from 0.05 mg/l to 0.3 mg/l.

21. The method of claim 20, wherein configuring the electrolytic generator to provide the at least one chlorine-based antifouling species comprises connecting a controller to the electrolytic generator.

* * * * *